United States Patent
Cuba Gyllensten et al.

(10) Patent No.: US 10,638,980 B2
(45) Date of Patent: May 5, 2020

(54) SYSTEM AND METHOD FOR PREDICTING HEART FAILURE DECOMPENSATION

(71) Applicant: KONINKLIJKE PHILIPS N.V., Eindhoven (NL)

(72) Inventors: Illapha Gustav Lars Cuba Gyllensten, Stockholm (SE); Rohan Joshi, Eindhoven (NL); Herman Jan ter Horst, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 218 days.

(21) Appl. No.: 15/284,575

(22) Filed: Oct. 4, 2016

(65) Prior Publication Data

US 2017/0100079 A1    Apr. 13, 2017

Related U.S. Application Data (60) Provisional application No. 62/240,702, filed on Oct. 13, 2015.

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0205* (2013.01); *A61B 5/7264* (2013.01); *A61B 5/021* (2013.01); *A61B 5/024* (2013.01)

(58) Field of Classification Search
CPC ....... A61B 5/0205; A61B 5/021; A61B 5/024; A61B 5/7264; A61B 5/7275;
(Continued)

(56) References Cited

U.S. PATENT DOCUMENTS

| 7,308,309 B1 | 12/2007 | Koh |
| 2003/0093125 A1 | 5/2003 | Zhu et al. |

(Continued)

FOREIGN PATENT DOCUMENTS

| WO | 2009036329 A1 | 3/2009 |
| WO | 2011126823 A1 | 10/2011 |

OTHER PUBLICATIONS

Henriques et al, "Prediction of Heart Failure Decompensation Events by Trend Analysis of Telemonitoring Data", IEEE Jouronal of Biomedical and Health Informatics, vol. 19, No. 5, Sep. 2015, pp. 1757-1769.

(Continued)

*Primary Examiner* — Deborah L Malamud (57) ABSTRACT

The present disclosure pertains to a system configured to predict decompensation in a subject with heart failure. The system comprises one or more hardware processors configured by machine-readable instructions to receive weight information, blood pressure information, and heart rate information about the subject; determine one or more weight parameters, one or more blood pressure parameters, and one or more heart rate parameters based on the received information; and predict decompensation in the subject based on the one or more weight parameters, the one or more blood pressure parameters, and the one or more heart rate parameters. Prior art systems use weight parameters alone for such prediction. However, weight parameters alone are often not predictive of decompensation.

18 Claims, 8 Drawing Sheets

(51) Int. Cl.
*A61B 5/021* (2006.01)
*A61B 5/024* (2006.01)

(58) Field of Classification Search
CPC ... A61B 5/0402; A61B 5/7282; A61B 5/0004; A61B 5/02; A61B 5/0245; A61B 5/486; A61B 2562/0247; A61B 5/04012; A63B 2230/30; G06F 19/3418; G06F 19/345; G06F 19/3431; G06F 19/3437; A61N 1/3621; A61N 1/3627; A61N 1/36514; A61N 1/36564; G06Q 50/22
See application file for complete search history.

(56) References Cited

U.S. PATENT DOCUMENTS

| | | | |
|---|---|---|---|
| 2007/0142732 | A1 | 6/2007 | Brockway et al. |
| 2008/0157980 | A1 | 7/2008 | Sachanandani et al. |
| 2009/0076401 | A1 | 3/2009 | Mazar et al. |
| 2010/0073170 | A1 | 3/2010 | Siejko et al. |
| 2011/0245711 | A1 | 10/2011 | Katra et al. |
| 2012/0253207 | A1* | 10/2012 | Sarkar ............... G06F 19/3431 600/483 |
| 2013/0116578 | A1 | 5/2013 | An et al. |
| 2014/0207493 | A1 | 7/2014 | Sarrafzadeh et al. |
| 2015/0157273 | A1 | 6/2015 | An et al. |

OTHER PUBLICATIONS

Sarkar, "A Dynamic Risk Score to Identify Increased Risk for Heart Failure Decompensation", IEEE Transactions on Biomedical Engineering, vol. 60, No. 1, Jan. 2013, pp. 147-150.

Zhang et al, "Predicting Hospitalization Due to Worsening Heart Failure Using Daily Weight Measurement: Analysis of the Trans-European Network-Home-Care Management System (TEN-HMS) Study", European Journal of Heart Failure, vol. 11, 2009, pp. 420-427.

* cited by examiner

SYSTEM AND METHOD FOR PREDICTING HEART FAILURE DECOMPENSATION

CROSS-REFERENCE TO PRIOR APPLICATIONS

This application claims the benefit of or priority of U.S. patent application Ser. No. 62/240,702, filed on Oct. 13, 2015, which is incorporated herein in whole by reference.

BACKGROUND

1. Field

The present disclosure pertains to a system and method for identifying and/or predicting decompensation in a subject with heart failure.

2. Description of the Related Art

Detecting decomposition in heart failure patients is known. Typically, decomposition in heart failure patients is detected based on weight change alone in the heart failure patient. For example, some episodes of heart failure are correlated with an increase in body weight as a result of water retention and this finding has been exploited as part of developing predictive models that 'recognize' decomposition. While the prognostic potential of an increase in weight prior to heart failure has been established, its sensitivity is quite poor and has not been used successfully to predict decomposition.

SUMMARY

Accordingly, one or more aspects of the present disclosure relate to a system configured to predict decompensation in a subject with heart failure. The system comprises one or more hardware processors and/or other components. The one or more hardware processors are configured by machine-readable instructions to: receive weight information that includes a weight of the subject generated by one or more weight sensors; receive blood pressure information that includes a blood pressure of the subject generated by one or more blood pressure sensors; receive heart rate information that includes a heart rate of the subject generated by one or more heart rate sensors; determine one or more weight parameters associated with a change in the weight of the subject based on the weight information; determine one or more blood pressure parameters associated with a change in the blood pressure of the subject based on the blood pressure information; determine one or more heart rate parameters associated with a change in the heart rate of the subject based on the heart rate information; and predict decompensation in the subject based on the one or more weight parameters, the one or more blood pressure parameters, and the one or more heart rate parameters.

Another aspect of the present disclosure relates to a method for predicting decompensation in a subject with heart failure with a prediction system. The system comprises one or more hardware processors and/or other components. The method comprises: receiving, with the one or more hardware processors, weight information that includes a weight of the subject generated by one or more weight sensors; receiving, with the one or more hardware processors, blood pressure information that includes a blood pressure of the subject generated by one or more blood pressure sensors; receiving, with the one or more hardware processors, heart rate information that includes a heart rate of the subject generated by one or more heart rate sensors; determining, with the one or more hardware processors, one or more weight parameters associated with a change in the weight of the subject based on the weight information; determining, with the one or more hardware processors, one or more blood pressure parameters associated with a change in the blood pressure of the subject based on the blood pressure information; determining, with the one or more hardware processors, one or more heart rate parameters associated with a change in the heart rate of the subject based on the heart rate information; and predicting, with the one or more hardware processors, decompensation in the subject based on the one or more weight parameters, the one or more blood pressure parameters, and the one or more heart rate parameters.

Still another aspect of present disclosure relates to a system for predicting decompensation in a subject with heart failure. The system comprises means for receiving weight information that includes a weight of the subject generated by one or more weight sensors; means for receiving blood pressure information that includes a blood pressure of the subject generated by one or more blood pressure sensors; means for receiving heart rate information that includes a heart rate of the subject generated by one or more heart rate sensors; means for determining one or more weight parameters associated with a change in the weight of the subject based on the weight information; means for determining one or more blood pressure parameters associated with a change in the blood pressure of the subject based on the blood pressure information; means for determining one or more heart rate parameters associated with a change in the heart rate of the subject based on the heart rate information; and means for predicting decompensation in the subject based on the one or more weight parameters, the one or more blood pressure parameters, and the one or more heart rate parameters.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
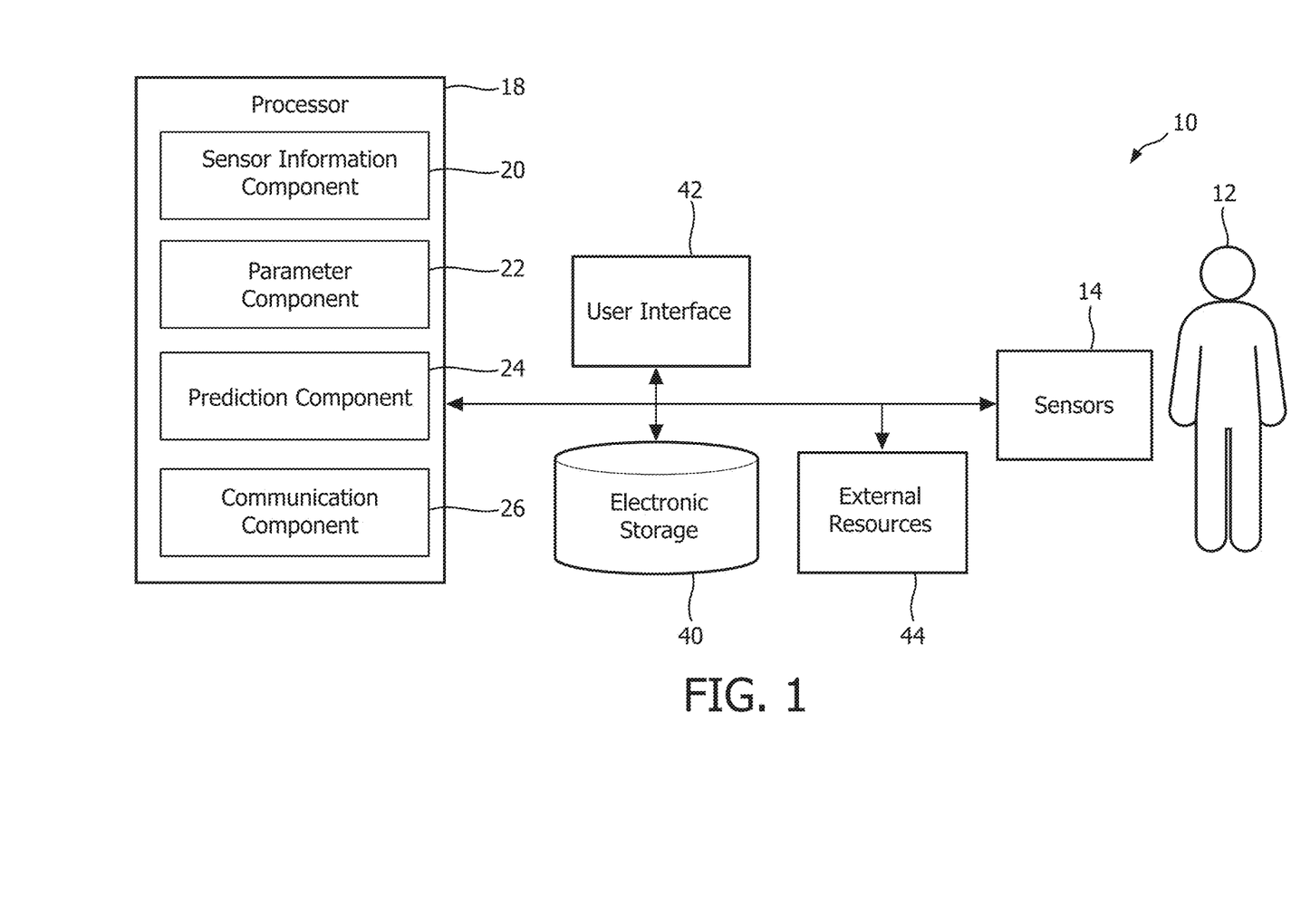
FIG. 1 is a schematic illustration of a system configured to predict decompensation in a subject with heart failure.

FIG. 1 is a schematic illustration of a system 10 configured to identify and/or predict decompensation in a subject 12 with heart failure. Heart failure is a chronic condition that arises due to abnormalities in cardiac structure and/or function. Heart failure is difficult to manage and is associated with a high rate of re-hospitalization and has a poor prognosis. Heart failure patients may experience a period of worsening hear failure symptoms until they eventually require hospitalization. This deterioration, also known as decompensation, may be non-acute initially. As such, there is a window of opportunity during which decompensation itself and/or upcoming decompensation is reflected in physiological signals of subject 12.

System 10 is configured to facilitate early intervention and treatment (with pharmaceutical therapy, timely lifestyle interventions, patient education, etc.) of heart failure patients (e.g., subject 12) before the heart failure patients require hospitalization. System 10 improves patient outcomes and also reduces costs and the burden on healthcare systems by keeping patients stable, among other advantages. System 10 is configured to automatically analyze physiological information about subject 12 (e.g., weight information, blood pressure information, heart rate information) and identify and/or predict decompensation in subject 12. System 10 may be located locally at or near subject 12 (e.g., located in the home of subject 12) and/or remotely from subject 12 (e.g., system 10 may comprise a remotely located server that receives information wireless transmitted from sensors that generate output signals that convey information about the vital signs of subject 12).

In some embodiments, system 10 comprises one or more of a sensor 14, a hardware processor 18, electronic storage 40, a user interface 42, external resources 44, and/or other components. For example, in some embodiments, system 10 may comprise sensor 14, processor 18, electronic storage 40, user interface 42, and external resources 44. In some embodiments, system 10 may comprise processor 18 by itself.

Sensors 14 are configured to generate output signals conveying information related to one or more vital signs of subject 12 and/or other information. The vital signs of subject 12 include vital signs related to weight of subject 12, blood pressure of subject 12, heart rate of subject 12, and/or other physiological parameters of subject 12. In some embodiments, sensors 14 generate output signals that convey such information alone and/or in combination with other physiological parameters of subject 12 such as blood chemistry of subject 12, hydration of subject 12, a respiration rate/output of subject 12, a blood oxygen level of subject 12, skin conductance and/or skin temperature of subject 12, body temperature of subject 12, the joint/muscular flexibility of subject 12, the blood circulation of subject 12, the cardiac output of subject 12, the relative health and/or sickness of subject 12, brain activity of subject 12, and/or other parameters. Sensors 14 may comprise one or more sensors that measure such parameters directly. For example, sensors 14 may be and/or include a heart rate sensor located on the chest of subject 12. Sensors 14 may comprise one or more sensors that generate output signals conveying information related to vital signs of subject 12 indirectly. For example, one or more sensors 14 may generate an output with vital signs information based on movement of subject 12 (e.g. movement detected via actigraphy signals from a bracelet on a wrist of subject 12 may indicate a higher heart rate). In some embodiments, sensors 14 may be and/or include one or more of a heart rate monitor, a blood pressure monitor, a weight scale, and/or other sensors.

Although sensors 14 are illustrated at a single location near subject 12, this is not intended to be limiting. Sensors 14 may include sensors disposed in a plurality of locations, such as for example, within and/or in communication with other components of system 10 (e.g., user interface 16 and/or processor 18 that are part of a smartphone associated with subject 12), coupled (in a removable manner) with clothing of subject 12, worn by subject 12 (e.g., as a headband, wristband, etc.), positioned to point at subject 12 (e.g., a camera that conveys output signals related to heart rate of subject 12), and/or in other locations. Sensors 14 may generate output signals continuously, at predetermined intervals, responsive to presence of and/or interaction with subject 12, and/or at other times.

Processor 18 is configured to provide information processing capabilities in system 10. As such, processor 18 may comprise one or more of a digital processor, an analog processor, a digital circuit designed to process information, an analog circuit designed to process information, a state machine, and/or other mechanisms for electronically processing information. Although processor 18 is shown in FIG. 1 as a single entity, this is for illustrative purposes only. In some embodiments, processor 18 may comprise a plurality of processing units. These processing units may be physically located within the same device (e.g., a server), or processor 18 may represent processing functionality of a plurality of devices operating in coordination (e.g., a server; computing devices associated with caregivers, subject 12 and/or other users; sensors 14, user interface 42, devices that are part of external resources 44, and/or other devices.)

As shown in FIG. 1, processor 18 is configured via machine-readable instructions to execute one or more computer program components. The one or more computer program components may comprise one or more of a sensor information component 20, a parameter component 22, a prediction component 24, a communication component 26, and/or other components. Processor 18 may be configured to execute components 20, 22, 24, and/or 26 by software; hardware; firmware; some combination of software, hardware, and/or firmware; and/or other mechanisms for configuring processing capabilities on processor 18.

It should be appreciated that although components 20, 22, 24, and 26 are illustrated in FIG. 1 as being co-located within a single processing unit, in embodiments in which processor 18 comprises multiple processing units, one or more of components 20, 22, 24, and/or 26 may be located remotely from the other components. The description of the functionality provided by the different components 20, 22, 24, and/or 26 described below is for illustrative purposes, and is not intended to be limiting, as any of components 20, 22, 24, and/or 26 may provide more or less functionality than is described. For example, one or more of components 20, 22, 24, and/or 26 may be eliminated, and some or all of its functionality may be provided by other components 20, 22, 24, and/or 26. As another example, processor 18 may be configured to execute one or more additional components that may perform some or all of the functionality attributed below to one of components 20, 22, 24, and/or 26.

Sensor information component 20 is configured to receive weight information, blood pressure information, heart rate information, and/or other information about subject 12 and/or other users. The weight information includes a weight of subject 12 generated by one or more weight sensors 14 and/or other information. The blood pressure information includes a blood pressure of subject 12 generated by one or more blood pressure sensors 14 and/or other information. The heart rate information includes a heart rate of subject 12 generated by one or more heart rate sensors 14 and/or other information. In some embodiments, the weight information, the blood pressure information, and/or the heart rate information is received directly from sensors 14 and/or other devices. In some embodiments, the weight information, the blood pressure information, and/or the heart rate information is received indirectly from sensors 14 and/or other devices via a database and/or other external resources 44 for example. In some embodiments, receiving the weight information, the blood pressure information, and the heart rate information includes actively obtaining the weight information, the blood pressure information, and/or the heart rate information from the sensors, external resources 44, and/or from other locations.

For example, sensors 14 may be configured to transmit (e.g., wired or wirelessly) information directly to sensor information component 20. In some embodiments, information may be transmitted to sensor information component 20 from a remotely located database that is part of external resources 44, for example. In some embodiments, sensor information component 20 may obtain information from a database, sensors 14, and/or other resources by electronically querying and/or requesting information from such devices and receiving the information in response. It should be noted that these examples are not intended to be limiting. Sensor information component 20 is configured to receive and/or obtain the weight information, the blood pressure information, the heart rate information, and/or any other information in any way that allows system 10 to function as described herein.

Parameter component 22 is configured to determine one or more weight parameters, one or more blood pressure parameters, one or more heart rate parameters, and/or other physiological parameters of subject 12. In some embodiments, the one or more weight parameters are associated with a change in the weight and/or other features of the weight of subject 12, and are determined based on the weight information from sensors 14 and/or other information. The one or more blood pressure parameters are associated with a change in the blood pressure and/or other features of the blood pressure of subject 12, and are determined based on the blood pressure information from sensors 14 and/or other information. The one or more heart rate parameters are associated with a change in the heart rate and/or other features of the heart rate of subject 12, and are determined based on the heart rate information from sensors 14 and/or other information.

In some embodiments, the one or more weight parameters include one or more of a change in mean weight of the subject during an immediately previous week, a change in mean weight of the subject during an immediately previous two weeks, a change in mean weight of the subject during an immediately previous month, a weight-based moving average convergence divergence with a long term window size of 40 days and a short term window size of 5 days, and/or other parameters. In some embodiments, the one or more blood pressure parameters include one or more of a systolic blood pressure-based moving average convergence divergence with a long term window size of 40 days and a short term window size of 5 days, a systolic blood pressure-based standard score with a sample length of 20 days, a systolic blood pressure-based standard score with a sample length of 40 days, a change in a mean diastolic blood pressure during an immediately previous week, a diastolic blood pressure-based standard score with a sample length of 20 days, and/or other parameters. In some embodiments, the one or more heart rate parameters include one or more of a change in mean heart rate during an immediately previous month, a heart rate-based moving average convergence divergence with a long term window size of 20 days a and a short term window size of 5 days, a heart rate-based moving average convergence divergence with a long term window size of 40 days and a short term window size of 5 days, a pulse pressure-based moving average convergence divergence with a long term window size of 20 days and a short term window size of 5 days, and/or other parameters.

It should be noted that the window sizes described above are not intended to be limiting. They are representative examples of window sizes for the various parameters. This disclosure contemplates window sizes of other lengths. The window sizes may have any length of time that allows the system to function as described herein.

Prediction component 24 is configured to identify and/or predict decompensation in subject 12. Decompensation is predicted based on the one or more weight parameters, the one or more blood pressure parameters, the one or more heart rate parameters, and/or other parameters. In some embodiments, decompensation is predicted based on at least one weight parameter, at least one blood pressure parameter, and at least one heart rate parameter. In some embodiments, predicting decompensation includes using the one or more weight parameters, the one or more blood pressure parameters, the one or more heart rate parameters, and/or other parameters as feature inputs in a Naïve Bayes classifier. The Naïve Bayes classifier may determine a predictive strength of individual parameters. For example, the predictive strength of the parameters may be estimated by kernel density estimation from the observed decompensations and/or other information. These could then be combined into a classification of decompensation risk in a Naïve Bayesian classifier.

In some embodiments, prediction component 24 is configured to identify and/or predict decompensation for subject 12 based on individual parameters with higher predictive strength relative to individual parameters with lower predictive strength. In some embodiments, prediction component 24 is configured to identify and/or predict decompensation based on at least one predictive weight parameter, at least one predictive blood pressure parameter, and at least one predictive heart rate parameter.

Examples of predictive weight parameters include one or more of a change in mean weight of the subject during an immediately previous week, a change in mean weight of the subject during an immediately previous two weeks, a change in mean weight of the subject during an immediately previous month, and/or a weight-based moving average convergence divergence with a long term window size of 40 days and a short term window size of 5 days (e.g., the weight parameters described above with respect to parameter component 22). Examples of predictive blood pressure parameters include one or more of a systolic blood pressure-based moving average convergence divergence with a long term window size of 40 days and a short term window size of 5 days, a systolic blood pressure-based standard score with a sample length of 20 days, a systolic blood pressure-based standard score with a sample length of 40 days, a change in a mean diastolic blood pressure during an immediately previous week, or a diastolic blood pressure-based standard score with a sample length of 20 days (e.g., the blood pressure parameters described above with respect to parameter component 22). Examples of predictive heart rate parameters include one or more of a change in mean heart rate during an immediately previous month, a heart rate-based moving average convergence divergence with a long term window size of 20 days a and a short term window size of 5 days, a heart rate-based moving average convergence divergence with a long term window size of 40 days and a short term window size of 5 days, or a pulse pressure-based moving average convergence divergence with a long term window size of 20 days and a short term window size of 5 days (e.g., the heart rate parameters described above with respect to parameter component 22).

In some embodiments, prediction component 24 is configured to generate (e.g., via machine learning, a neural network, and/or other methods) a decompensation prediction model (e.g., algorithm) and identify and/or predict decompensation in subject 12 based on the prediction model. The predictive parameters described above and/or other parameters may be inputs to such a model. Predication component 24 may determine and/or adjust a weight of individual parameters to adjust an amount of influence a particular parameter has on the identification/prediction. Prediction component 24 may identify and/or predict decompensation in subject 12 based on these weighted parameters and the prediction model. In some embodiments, prediction component 24 is configured to identify and/or predict decompensation in subject 12 based on changes in the predictive parameters over time. For example, prediction component 24 may generate a graphical representation of one or more of the predictive parameters over time. Prediction component 24 may identify and/or predict decompensation in subject 12 based on a change in slope of one or more graphical lines representing one or more of the predictive parameters over time. In some embodiments, prediction component 24 is configured such that predicting decompensation includes generating a decompensation risk score that increases with increasing risk of decompensation, and determining whether the decompensation risk score breaches a decompensation risk threshold level. The decompensation risk score may be an output of the prediction model, for example, it may be a slope of a graphical line representing a parameter over time, and/or may be determined in other ways. In some embodiments, individual parameter values may be associated with an individual risk estimate (see examples f-3 in FIG. 7, f-4 in FIG. 8 and f-11 in FIG. 9, and in Table I below). These can then be combined into a joint risk estimate.

Communication component 26 is configured to communicate identified and/or predicted decompensation to subject 12, a caregiver of subject 12, and/or other people. Communication component 26 is configured to communicate via user interface 42, via email, via text messages, via a website, via a phone call, and or with other forms of communication. For example, in some embodiments, communication component 26 causes user interface 16 to display information (e.g., an alert indication) that communicates identified and/or predicted decompensation to the caregiver, subject 12, and/or other people. In some embodiments, communication component 26 is configured to send an email or a text with such information to the caregiver, subject 12, and/or other people. By way of a non-limiting example, a caregiver may then determine whether or not to follow up with subject 12 (e.g., in person, on the phone, etc.), arrange additional support for the individual, and/or take other actions. As another example, subject 12 may decide to visit the hospital based on the communication from communication component 26.

Electronic storage 40 comprises electronic storage media that electronically stores information. The electronic storage media of electronic storage 40 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 40 may be (in whole or in part) a separate component within system 10, or electronic storage 40 may be provided (in whole or in part) integrally with one or more other components of system 10 (e.g., user interface 44, processor 18, etc.). In some embodiments, electronic storage may be located in a server together with processor 18, in a server that is part of external resources 44, in a computing device associated with subject 12 and/or other users, and/or in other locations. Electronic storage 40 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 40 may store software algorithms, information determined by processor 18, information received via user interface 42 and/or external computing systems, information received from external resources 44, information received from sensors 14, and/or other information that enables system 10 to function as described herein.

User interface 42 is configured to receive information from and/or provide information to one or more users (e.g., subject 12, caregivers, etc.) of system 10. User interface 42 is configured to provide an interface between system 10 and caregivers, subject 12, and/or other users through which caregivers, subject 12, and/or other users may provide information to and receive information from system 10. This enables data, cues, results, and/or instructions and any other communicable items, collectively referred to as "information," to be communicated between a user (e.g., a caregiver, subject 12, and/or other users) and processor 18, and/or other components of system 10. For example, identified and/or predicted decompensation, and/or other information may be communicated from system 10 to a caregiver, subject 12, and/or other users via user interface 42.

Examples of interface devices suitable for inclusion in user interface 42 comprise a graphical user interface, a display, a touchscreen, a keypad, buttons, switches, a keyboard, knobs, levers, speakers, a microphone, an indicator light, an audible alarm, a printer, a haptic feedback device, and/or other interface devices. In some embodiments, user interface 42 comprises a plurality of separate interfaces. For example, user interface 42 may comprise a plurality of different interfaces associated with a plurality of computing devices associated with different caregivers; an interface that is part of a computing device associated with subject 12; an interface associated with processor 18, electronic storage 40, external resources 44, sensors 14, and/or other components of system 10; an interface included in a server that also includes processor 18 and/or electronic storage 40; and/or other interfaces. User interface 42 is configured such that the plurality of caregivers may provide information to and receive information from system 10 via the individual ones of the plurality of user interfaces. In some embodiments, user interface 42 comprises at least one interface that is provided integrally with processor 18 and/or other components of system 10.

It is to be understood that other communication techniques, either hard-wired or wireless, are also contemplated by the present disclosure as user interface 42. For example, the present disclosure contemplates that user interface 42 may be integrated with a removable storage interface provided by electronic storage 40. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 16 comprise, but are not limited to, an RS-232 port, RF link, an IR link, modem (telephone, cable or other). In short, any technique for communicating information with system 10 is contemplated by the present disclosure as user interface 16.

External resources 44 may include sources of information (e.g., databases, websites, etc.), external entities participating with system 10 (e.g., a medical records system of a health care provider), medical equipment configured to communicate with external systems, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 30 may be provided by resources included in system 10. External resources 44 may be configured to communicate with sensors 14, processor 18, electronic storage 40, user interface 42, and/or other components of system 10 via wired and/or wireless connections, via a network (e.g., a local area network and/or the internet), via cellular technology, via Wi-Fi technology, and/or via other resources.

Figure 2:
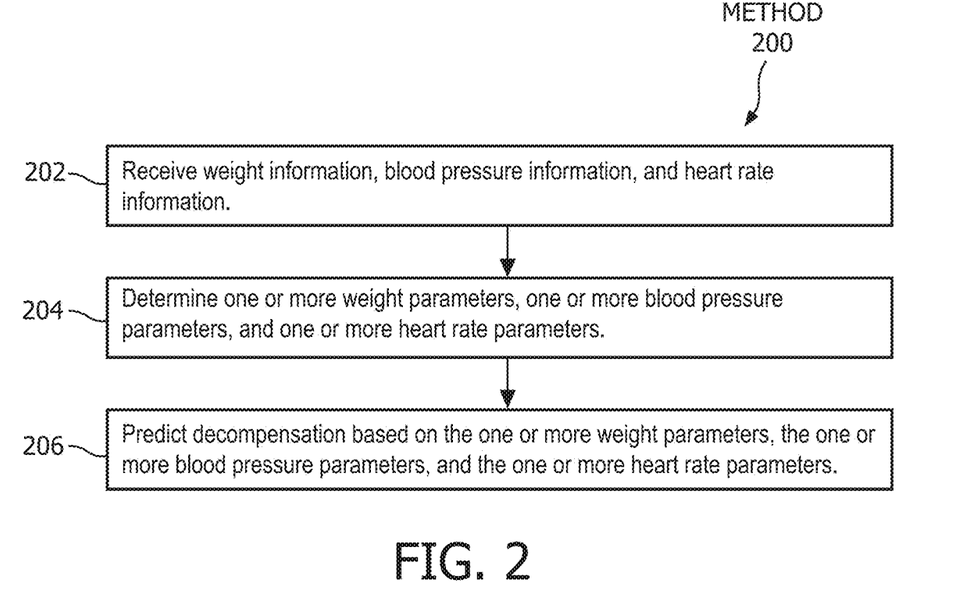
FIG. 2 illustrates a method for predicting decompensation in a subject with heart failure.

FIG. 2 illustrates a method 200 for predicting decompensation in a subject with heart failure with a prediction system. The system comprises one or more one or more sensors, one or more user interfaces, electronic storage, external resources, one or more hardware processors, and/or other components. The one or more hardware processors are configured to execute computer program components. The computer program components comprise a sensor information component, a parameter component, a prediction component, a communication component, and/or other components. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 2 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, weight information, blood pressure information, and heart rate information is received. The weight information includes a weight of the subject generated by one or more weight sensors. The blood pressure information includes a blood pressure of the subject generated by one or more blood pressure sensors. The heart rate information includes a heart rate of the subject generated by one or more heart rate sensors. In some embodiments, the weight information, the blood pressure information, and/or the heart rate information is received directly from the sensors. In some embodiments the weight information, the blood pressure information, and/or the heart rate information is received indirectly from the sensors via a database and/or other external resources for example. In some embodiments, receiving the weight information, the blood pressure information, and the heart rate information includes actively obtaining the weight information, the blood pressure information, and/or the heart rate information from the sensors, the database and/or the other external resources. In some embodiments, operation 202 is performed by a processor component the same as or similar to sensor information component 20 (shown in FIG. 1 and described herein).

At an operation 204, one or more weight parameters, one or more blood pressure parameters, and one or more heart rate parameters are determined. The one or more weight parameters are associated with a change in the weight of the subject and are determined based on the weight information. The one or more blood pressure parameters are associated with a change in the blood pressure of the subject and are determined based on the blood pressure information. The one or more heart rate parameters are associated with a change in the heart rate of the subject and are determined based on the heart rate information.

In some embodiments, the one or more weight parameters include one or more of a change in mean weight of the subject during an immediately previous week, a change in mean weight of the subject during an immediately previous two weeks, a change in mean weight of the subject during an immediately previous month, or a weight-based moving average convergence divergence with a long term window size of 40 days and a short term window size of 5 days. In some embodiments, the one or more blood pressure parameters include one or more of a systolic blood pressure-based moving average convergence divergence with a long term window size of 40 days and a short term window size of 5 days, a systolic blood pressure-based standard score with a sample length of 20 days, a systolic blood pressure-based standard score with a sample length of 40 days, a change in a mean diastolic blood pressure during an immediately previous week, or a diastolic blood pressure-based standard score with a sample length of 20 days. In some embodiments, the one or more heart rate parameters include one or more of a change in mean heart rate during an immediately previous month, a heart rate-based moving average convergence divergence with a long term window size of 20 days a and a short term window size of 5 days, a heart rate-based moving average convergence divergence with a long term window size of 40 days and a short term window size of 5 days, or a pulse pressure-based moving average convergence divergence with a long term window size of 20 days and a short term window size of 5 days.

In some embodiments, operation 204 is performed by a processor component the same as or similar to parameter component 22 (shown in FIG. 1 and described herein).

At an operation 206, decompensation is predicted. Decompensation is predicted based on the one or more weight parameters, the one or more blood pressure parameters, and the one or more heart rate parameters. In some embodiments, operation 206 includes predicting decompensation using the one or more weight parameters, the one or more blood pressure parameters, and the one or more heart rate parameters as feature inputs in a Naïve Bayes classifier. In some embodiments, predicting decompensation includes generating a decompensation risk score that increases with increasing risk of decompensation, and determining whether the decompensation risk score breaches a decompensation risk threshold level. In some embodiments, operation 206 is performed by a processor component the same as or similar to prediction component 24 (shown in FIG. 1 and described herein).

System 10 and method 200 are based on the experimental procedure and data described below. The example experiment described below comprised retrospective analysis of two databases of 267 daily home telemonitored (e.g., remotely monitored) heart failure (HF) subjects. The best multivariate feature (parameter) set with a value of 0.70 for area under the curve (AUC) with a standard deviation (SD) of 0.01 comprises weight, systolic blood pressure (BP), and heartrate (HR) based features. The example experiment described below is not intended to be limiting.

Example Experimental Methods and Data

1. Patient Population

The data used for this study was retroactively collected from the Trans-European Network-Home-Care Management System (TEN-HMS) and from a telemonitoring service in Hull, UK (Motiva-Hull) in which patients with a recent admission for worsening HF could be enrolled. Amongst other criteria, the TEN-HMS study excluded subjects with a left ventricular ejection fraction (LVEF) greater than 40%. With the intention of homogenizing the two databases those patients in the Motiva-Hull database who (upon enrolment) presented with a LVEF greater than 40% and those without records for both LVEF and N-terminal pro-brain natriuretic peptide (NT-proBNP) from the time of enrolment were excluded. Subjects were required to use a telemonitoring device installed in their homes for recording their weight, BP and HR every day, at a fixed time. An individual instance of measurement led to a single value for weight, systolic BP, diastolic BP and HR. For the purpose of the study, in the case of multiple daily measurements, only the first measurement of the day was retained, while data corresponding to the days with no recordings was obtained after linear interpolation.

2. Selecting Cases of HF and Controls

In order to evaluate whether the physiological changes that lead up to cases of HF are distinctive, they were compared with natural variations from a stable period, hereafter referred to as 'control' cases. Since not all episodes of HF have sufficient telemonitored data in the days preceding hospitalization, not all cases were used for comparative analyses. For analysis, data from the 30-day window preceding HF is used, since this is the period during which physiological changes are expected to manifest. Therefore only those cases of HF that had at least 50% entries (empirical decision) in the 30-day and the eight-day windows that preceded hospitalization were retained. While data sufficiency in the days preceding HF is important, it is also necessary to ensure that the data is reflective of the impending HF and free from the influence of any past 'events' experienced by the patient. In order to avoid such 'contamination' only those instances of HF were retained where the 75 days preceding HF were free of other events. The mean values of the physiological signals between the 30th day and the 45th day preceding HF served as a 'stable baseline' reference for every subject.

For generating control cases, data sufficiency criteria, identical to those used for the cases of HF were applied at five random points (control 'events' including enrolment and/or discharge from previous hospitalization, for example) on the time-series data of all those subjects who did not experience an episode of HF leading to hospitalization (or death) during the period of monitoring (until censoring/death). Here too, a 'control-case' had to be at least 75 days away from enrolment in to the study or any past 'events'. These data, corresponding to both the cases of HF and the controls, were used to generate and test features.

Previously researched algorithms that have attempted to capture weight-gain preceding HF have had limited sensitivity. These results may be explained by quantifying the episodes of HF that do exhibit weight-gain preceding hospitalization. Weight-trends were stratified as 'uptrend', 'downtrend', or 'no trend', based on whether the mean weight in the ten days preceding HF increased by, decreased by, or stayed within one kilogram of the stable baseline value.

While the data preceding HF is relevant for analyzing the predictive potential of the different physiological signals, the post-discharge data can hold useful information on the stabilizing effects of hospitalization and the associated therapy. In order to observe this effect, certain data sufficiency criteria were applied to the stream of data following discharge (from treatment for HF). These criteria required at least 50% data in the ten-day and the 30-day window post discharge, along with the absence of 'events' in the 60 days post-discharge. Here, 'events' refers to HF leading to hospitalization or death.

Figure 3:
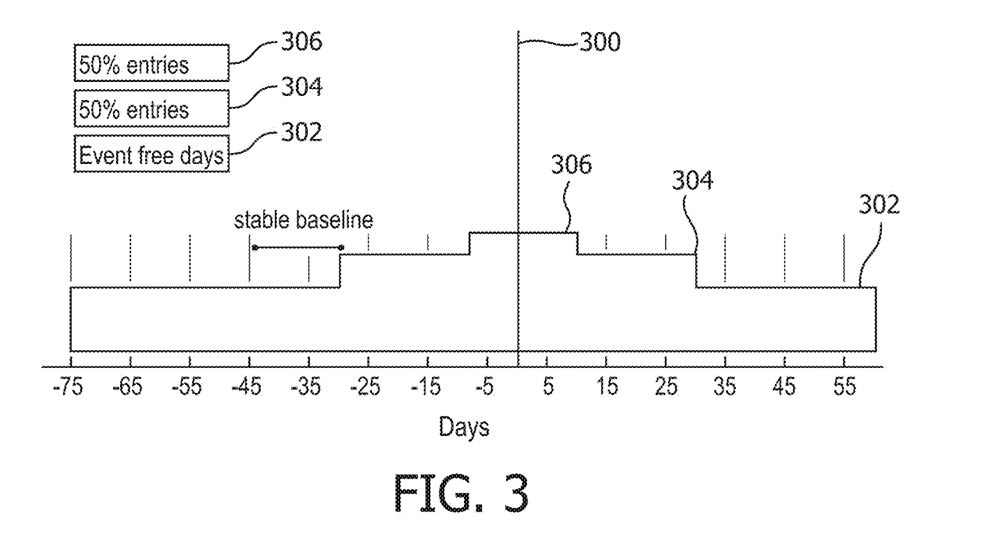
FIG. 3 illustrates experimental selection criteria that were applied to heart failure cases and controls in an example experiment.

FIG. 3 shows the selection criteria that were applied to the cases of HF and controls. FIG. 3 illustrates a line 300 representing admission to the hospital, during which no telemonitoring data is gathered, and the subsequent discharge. Section 302 represents the event-free period, while the sections 304 and 306 represent the periods of time with a requirement of at least 50% data entries. All cases that satisfied the pre-admission criteria were used for analysis while those that satisfied the post-discharge criteria too were used for visualizing the effect of hospitalization on the physiological signals.

3. Feature Generation

A battery of 48 features (e.g., parameters) were developed for evaluating the prognostic potential of time-series data of weight (16 features), systolic blood pressure (eight features), diastolic blood pressure (eight features), pulse pressure (eight features), and heart rate (eight features) for identifying periods of deteriorating HF. All features were developed from three 'families of features'.

The first feature-family was the rule-of-thumb algorithm that was motivated by the guideline thresholds of two kg weight gain in two-three days or two percent weight gain in two days. Such features were intended to capture acute discriminative changes in weight. Six weight-based features corresponding to one, two and three day differences in absolute and percentage weight change were employed. Since evidence of increase in weight staring up to a month before HF deterioration was available, features corresponding to the differences (absolute and percentage) between the mean weights measured over a week, a fortnight, and a month with respect to stable baseline values were also developed. This gave six features.

For systolic blood pressure (BP), diastolic blood pressure (BP), pulse pressure (PP), and heart rate (HR), four features apiece were developed to capture the absolute differences between the mean values measured over the past week, the penultimate week (this was an empirical choice motivated by observing a bump in the population-level systolic BP trend in the week penultimate to HF), the past fortnight and the past month with respect to stable baseline values.

The second feature-family used the moving average convergence divergence (MACD) algorithm, (e.g., the difference between the mean of short-term data (STWS—short-term window size) and a long-term average (LTWS—long-term window size)). The use of this feature-family was employed for weight, BP (systolic, diastolic and pulse pressure) and HR using LTWSs of 20 and 40 days respectively, along with an STWS of five days. In effect, the MACD algorithm acts like the combination of a differential operator and a low pass filter, and is intended to capture fast changes with respect to slower-changing trends.

The third feature-family was based on the standard score (SS), which was defined as:

$$SS(t) = (x(t) - \mu)/\sigma$$

where, x(t) is the value of the time series signal at time 't' while 'μ' and 'σ' are the mean and standard deviation, respectively, calculated from a predefined length of past values. SS-based features were employed for weight, BP (systolic, diastolic and pulse pressure) and HR using sample lengths of 20 and 40 days respectively. The SS-based features were designed to capture changes in a subject's physiological signals that differ significantly from the naturally exhibited variation of an individual. Both, the MACD and the SS-based features used the original, un-interpolated data.

4. Classification Approach

While decompensation is believed to be reflected in physiological changes, the precise point in time when such deterioration peaks prior to requiring hospitalization is unknown. Therefore, analysis was carried out using different lengths of data (2, 5, 8, and 12-day windows) from the subject's past measurements. In this scenario, the entire 'window of data' of a subject is considered to correspond to 'HF' or to a 'control', as the case may be.

The Naïve Bayes classifier was employed in Matlab (MathWorks) to distinguish daily data belonging to the period leading up to a HF from control periods. The class priors were defined to be uniform while the continuous data was represented by estimating the kernel density. The predictive strength of the classifier was evaluated by calculating the area under the curve (AUC) from the concatenated left out folds of a fivefold cross-validation stratified by HF and control data. This was carried out five times to provide an average CV-AUC estimate and estimates of its dispersion (standard deviation). In order to visualize the feature values that determine the different probabilities of decompensation, individual feature-probabilities contributing to the top performing model for a five-day window were estimated by fitting a fourth order polynomial to the test data using the linear least squares method.

5. Characteristics of the HF and the Control Subjects

One hundred and eleven (111) subjects (out of 267) presented with at least one episode of HF during the period of monitoring (until death/censoring). A total of 256 episodes of HF occurred in these 111 patients. The control-cohort comprised the 151 subjects (out of 267) who did not suffer from an episode of HF (or die due to HF) during the period of monitoring. No significant differences (p>0.05) were present in the baseline characteristics of the HF and the control cohorts with the exceptions of NT-proBNP and serum sodium values, which were higher and lower respectively in the HF-cohort. The lower serum sodium levels were perhaps due to greater water retention despite titrated diuretic therapy. Upon implementing the selection criteria described above, 50 instances of HF and 112 of controls were found to be suitable for quantitative analysis. These selected instances originated from 40 patients of the HF-cohort and 63 patients of the control-cohort.

6. Physiological Trends Preceding HF and Following Discharge

While 50 episodes of HF had fulfilled the pre-admission criteria, only 44 episodes of HF remained after applying the post-discharge criteria. These were used for visualizing the influence of hospitalization on physiological signals. Out of the five physiological signals considered, only weight changed visibly in the days leading up to HF and after discharge. A closer analysis of the weight trends, based on stratifying trends leading up to hospitalization (FIG. 4) shows that 41% of decompensation subjects did not exhibit any increase in weight prior to HF. In fact, weight decreased in 20% of the cases in the weeks prior to hospitalization with some increase, possibly edematous in nature, in the week immediately preceding HF.

Figure 4:
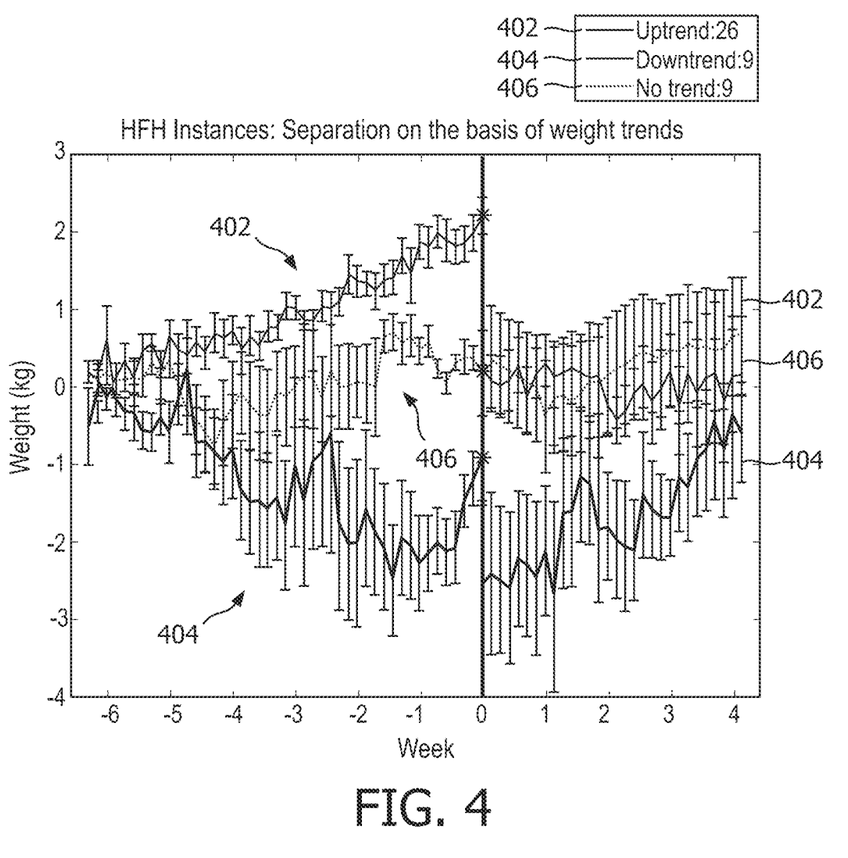
FIG. 4 illustrates separation of heart failure instances on the basis of weight trends in the example experiment.

In FIG. 4, stratification of the instances of HF on the basis of weight (stable baseline removed) shows an uptrend 402, a downtrend 404, or a flat/no trend 406 in the weeks preceding HF. These trends depict the mean population weight and the error bars represent the standard error of mean. The legend indicates the number of subjects in each subgroup. The line 400 represents admission to the hospital, during which no telemonitoring data is gathered, and the subsequent discharge.

7. Univariate Analysis

Figure 5:
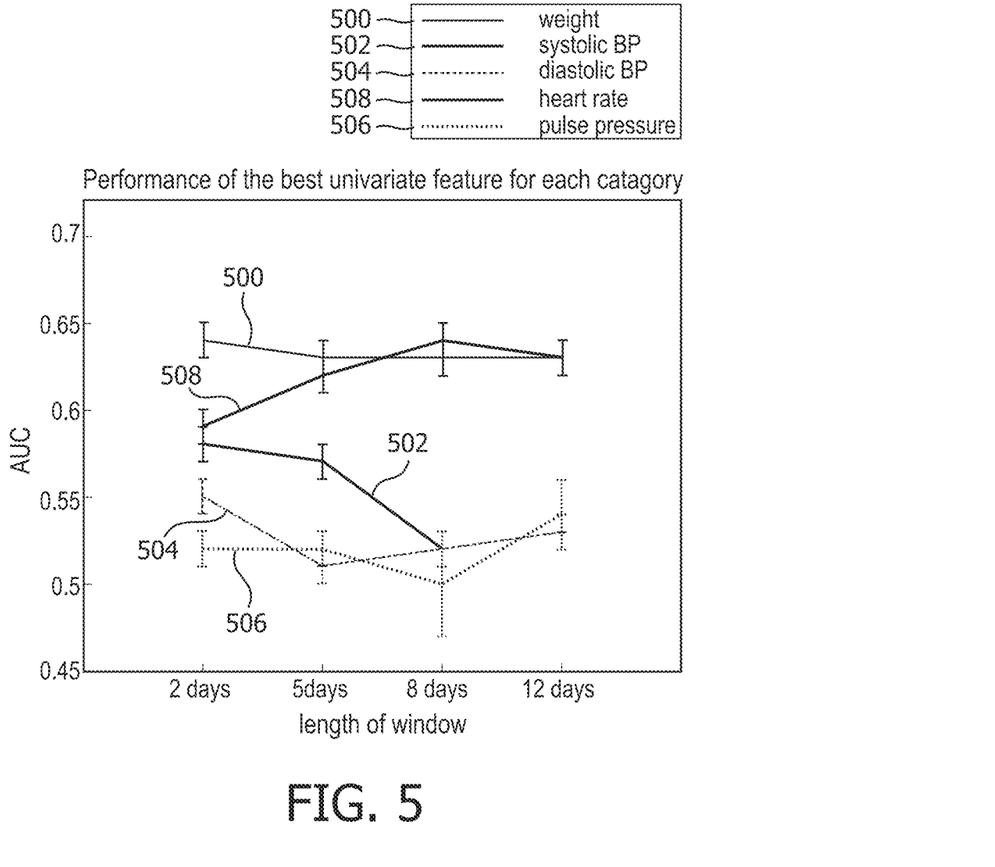
FIG. 5 illustrates AUC values of the best performing experimental features (e.g., parameters).

FIG. 5 indicates the AUC values of the best performing features (e.g. parameters) originating from weight 500, systolic BP 502, diastolic BP 504, PP 506, and HR 508 for window lengths of two, five, eight and 12 days. For univariate analysis, features originating from each of the five physiological signals were individually tested on the four different window lengths of data using the Naïve Bayes classifier. FIG. 5 shows the best performing features for each physiological category for all window lengths. Interestingly, while the performance of the best weight-based feature does not change much with longer windows, the best HR-based features become more discriminatory as window length increases, in fact outperforming the best weight-based feature for a window of eight days. The performance of the BP-based features is lower than that of weight and HR-based ones and tends to decrease with increasing window-lengths.

8. Multivariate Analysis

Figure 6:
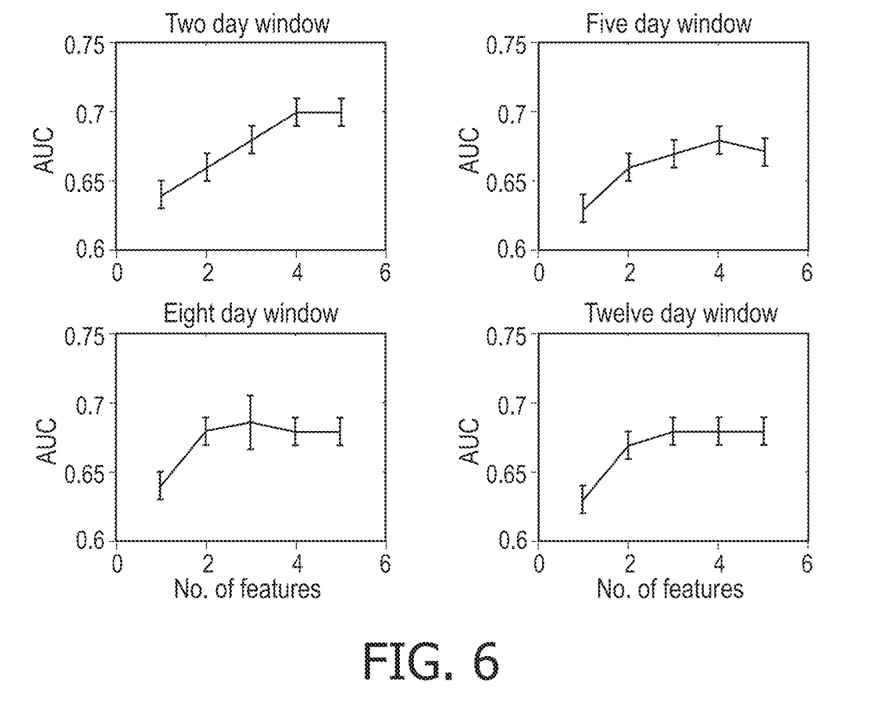
FIG. 6 illustrates AUC and the SD of AUC's for the best feature combinations for window lengths of 2, 5, 8, and 12 days.

FIG. 6 illustrates AUC and the SD of AUC's for the best feature combinations for window lengths of 2, 5, 8, and 12 days. Features are taken in combinations of one (equivalent to univariate) up to five at a time. For multivariate analysis, the best performing features from univariate analysis were retained for each category (weight, systolic BP, diastolic BP, PP and HR) and for each window. This led to 18 unique features/parameters (f-1 to f-18, see Table I below) that were then used in combinations of one feature up to five features at a time in order to examine the performance of the Naïve Bayes classifier. FIG. 6 shows the AUC's of the best performing feature combinations for all window lengths. The performance of the classifier improves as the number of features increase, up to a combination of four features, after which it levels off or deteriorates. This pattern is common to all window-lengths that were considered.

Referring to Table I below, for a two-day window, the combination of f-4, f-9, f-11, and f-12 yields the best results, while for a five-day window, the best result is provided by the combination of f-3, f-4, f-6, and f-11. The weight and HR-based feature combination of f-3, f-4, and f-11 give the best result for an eight-day window while f-2, f-4 and f-11 perform best for a 12-day window. The list of best performing (unique) features obtained from univariate analysis for each physiological signal and across all window lengths. The features that contribute to the best performing feature combinations in multivariate analysis, irrespective of window length are highlighted in bold.

TABLE I

Best Performing Features (Parameters) in Multi-variate Analysis

| Feature No. | Feature Definition |
| --- | --- |
| f-1 | Change in mean weight of the past week with respect to (w.r.t) baseline |
| f-2 | Change in mean weight of the past fortnight w.r.t baseline |
| f-3 | Change in mean weight of the past month w.r.t baseline |
| f-4 | Weight-based MACD with LTWS = 40 days, STWS = 5 days |
| f-5 | Systolic BP-based MACD with LTWS = 40 days, STWS = 5 days |
| f-6 | Systolic BP-based SS with sample length = 20 days |
| f-7 | Systolic BP-based SS with sample length = 40 days |
| f-8 | Change in mean diastolic BP of the past week w.r.t baseline |
| f-9 | Diastolic BP-based SS with sample length = 20 days |
| f-10 | Diastolic BP-based SS with sample length = 40 days |
| f-11 | Change in mean heart rate of the past month w.r.t baseline |
| f-12 | Heart rate-based MACD with LTWS = 20 days, and STWS = 5 days |
| f-13 | Heart rate-based MACD with LTWS = 40 days, and STWS = 5 days |
| f-14 | Heart rate-based SS with sample length = 20 days, |
| f-15 | Change in mean pulse pressure of the past month w.r.t baseline |
| f-16 | Pulse pressure-based MACD with LTWS = 20 days and STWS = 5 days |
| f-17 | Pulse pressure-based MACD with LTWS = 40 days and STWS = 5 days |
| f-18 | Pulse pressure-based SS with sample length = 40 days |

Figure 7:
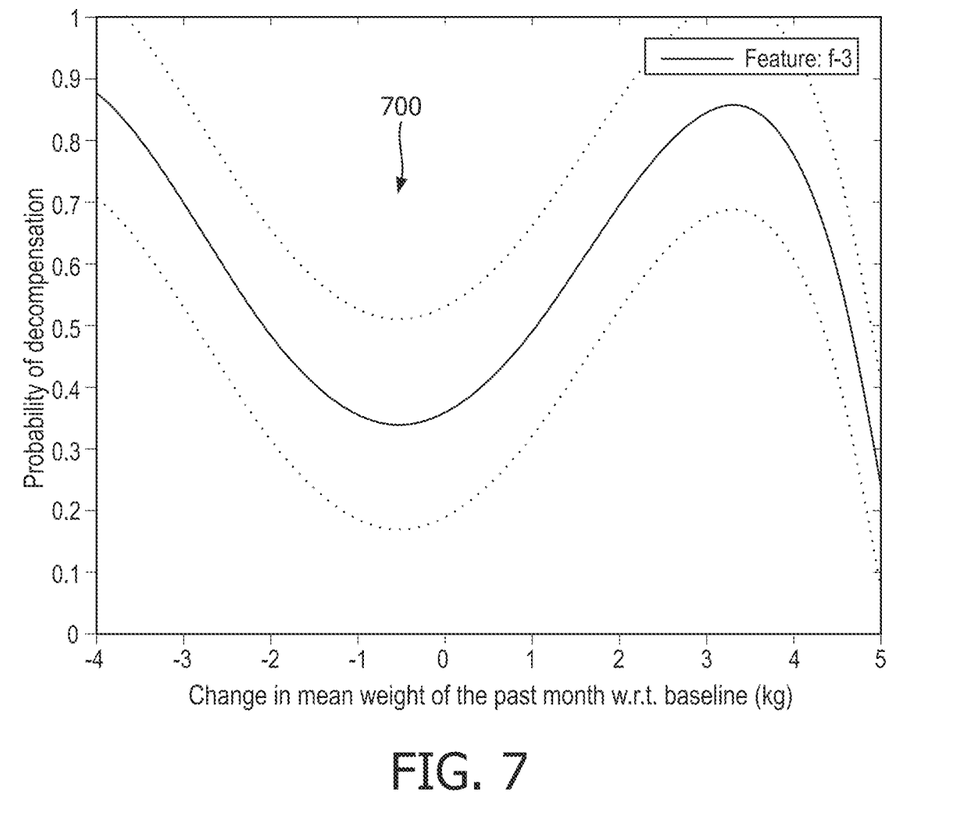
FIG. 7 illustrates an individual risk estimate for a first example feature (f-3).
Figure 8:
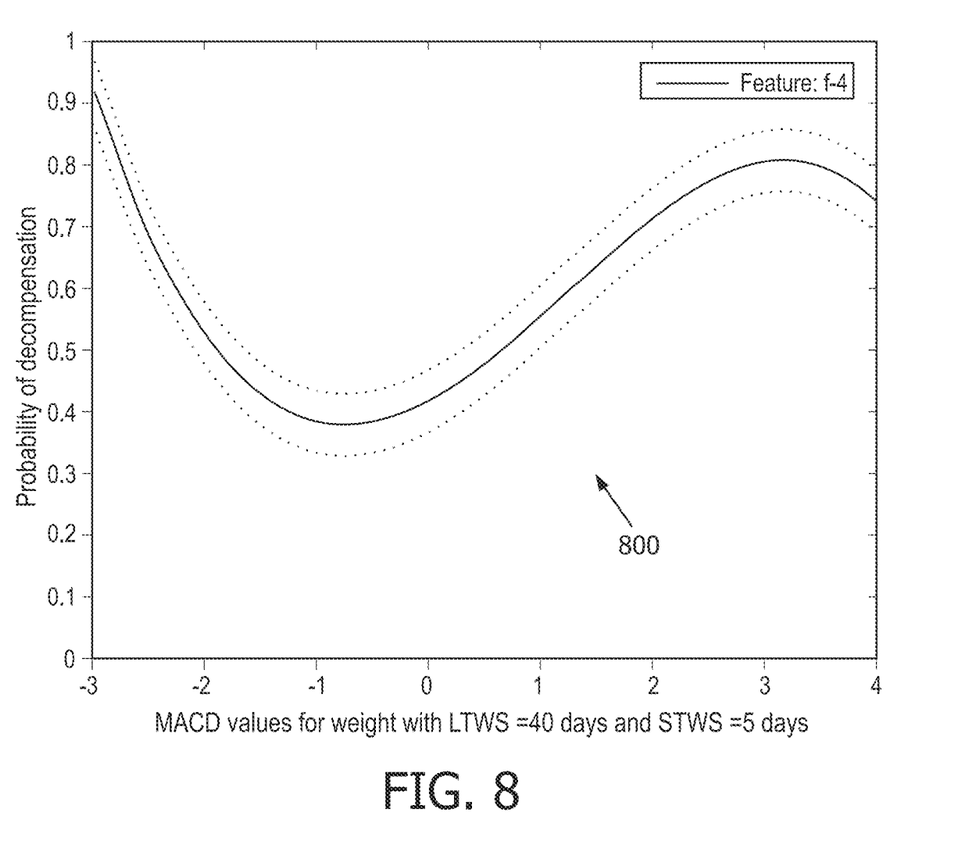
FIG. 8 illustrates an individual risk estimate for a second example feature (f-4).
Figure 9:
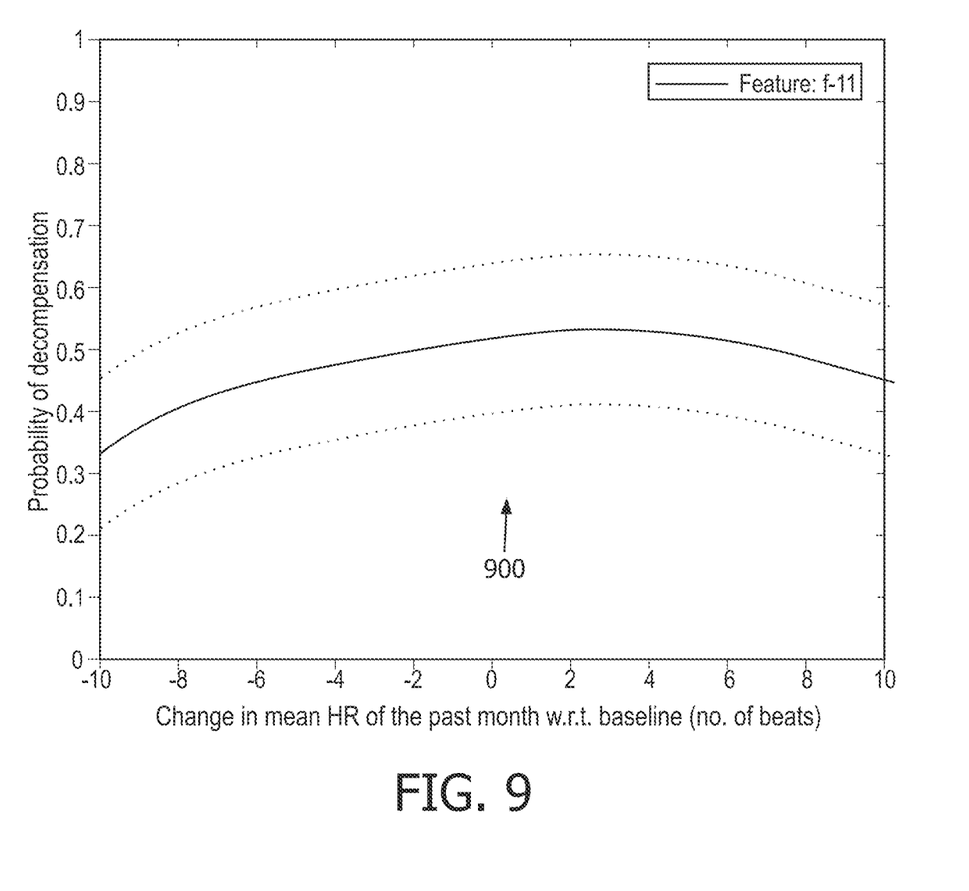
FIG. 9 illustrates an individual risk estimate for a third example feature (f-11).

As described above, in some embodiments, individual parameter values may be associated with an individual risk estimate. For example, an individual risk estimate 700 for f-3 is shown in FIG. 7. An individual risk estimate 800 for f-4 is shown in FIG. 8. An individual risk estimate 900 for f-11 is shown in FIG. 9. In some embodiments, these can then be combined into a joint risk estimate.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to predict decompensation in a subject with heart failure, the system comprising:
   one or more hardware processors configured by machine-readable instructions to:
      determine baseline information for the subject based on physiological data of other patients with heart failure, the physiological data of the other patients corresponding to a period of time when the other patients have stable physiological parameters that precedes heart failure;
   receive weight information that includes a weight of the subject generated by one or more weight sensors;

receive blood pressure information that includes a blood pressure of the subject generated by one or more blood pressure sensors;

receive heart rate information that includes a heart rate of the subject generated by one or more heart rate sensors;

determine one or more weight parameters associated with a change in the weight of the subject based on the weight information with respect to the baseline information;

determine one or more blood pressure parameters associated with a change in the blood pressure of the subject based on the blood pressure information with respect to the baseline information;

determine one or more heart rate parameters associated with a change in the heart rate of the subject based on the heart rate information with respect to the baseline information;

determine individual weight, blood pressure, and heart rate parameters with higher predictive strength for predicting decompensation relative to other weight, blood pressure, and heart rate parameters with lower predictive strength, the individual weight, blood pressure, and heart rate parameters with higher predictive strength comprising at least one predictive weight parameter, at least one predictive blood pressure parameter, and at least one predictive heart rate parameter; and predict decompensation in the subject based on the at least one weight parameter, the at least one blood pressure parameter, and the at least one heart rate parameter with higher predictive strength for predicting decompensation relative to the other weight, blood pressure, and heart rate parameters with lower predictive strength.

2. The system of claim 1, wherein the one or more hardware processors are further configured to predict decompensation using the one or more weight parameters, the one or more blood pressure parameters, and the one or more heart rate parameters as feature inputs in a Naïve Bayes classifier.

3. The system of claim 1, wherein the one or more hardware processors are further configured such that the one or more blood pressure parameters include one or more of a systolic blood pressure-based moving average convergence divergence with a long term window size of 40 days and a short term window size of 5 days, a systolic blood pressure-based standard score with a sample length of 20 days, a systolic blood pressure-based standard score with a sample length of 40 days, a change in a mean diastolic blood pressure during an immediately previous week, or a diastolic blood pressure-based standard score with a sample length of 20 days.

4. The system of claim 1, wherein the one or more hardware processors are further configured such that and the one or more heart rate parameters include one or more of a change in mean heart rate during an immediately previous month, a heart rate-based moving average convergence divergence with a long term window size of 20 days a and a short term window size of 5 days, a heart rate-based moving average convergence divergence with a long term window size of 40 days and a short term window size of 5 days, or a pulse pressure-based moving average convergence divergence with a long term window size of 20 days and a short term window size of 5 days.

5. The system of claim 1, wherein the one or more hardware processors are further configured such that predicting decompensation includes generating a decompensation risk score that increases with increasing risk of decompensation, and determining whether the decompensation risk score breaches a decompensation risk threshold level.

6. The system of claim 1, wherein the one or more hardware processors are configured such that the determination of which individual weight, blood pressure, and heart rate parameters have higher predictive strength is made based on changes in the individual weight, blood pressure, and heart rate parameters over time in the subject.

7. A method for predicting decompensation in a subject with heart failure the method comprising:

determining, with one or more hardware processors, baseline information for the subject based on physiological data of other patients with heart failure, the physiological data of the other patients corresponding to a period of time when the other patients have stable physiological parameters that precedes heart failure;

receiving, with the one or more hardware processors, weight information that includes a weight of the subject generated by one or more weight sensors;

receiving, with the one or more hardware processors, blood pressure information that includes a blood pressure of the subject generated by one or more blood pressure sensors;

receiving, with the one or more hardware processors, heart rate information that includes a heart rate of the subject generated by one or more heart rate sensors;

determining, with the one or more hardware processors, one or more weight parameters associated with a change in the weight of the subject based on the weight information;

determining, with the one or more hardware processors, one or more blood pressure parameters associated with a change in the blood pressure of the subject based on the blood pressure information;

determining, with the one or more hardware processors, one or more heart rate parameters associated with a change in the heart rate of the subject based on the heart rate information;

determining, with the one or more hardware processors, individual weight, blood pressure, and heart rate parameters with higher predictive strength for predicting decompensation relative to other weight, blood pressure, and heart rate parameters with lower predictive strength, the individual weight, blood pressure, and heart rate parameters with higher predictive strength comprising at least one predictive weight parameter, at least one predictive blood pressure parameter, and at least one predictive heart rate parameter; and predicting, with the one or more hardware processors, decompensation in the subject based on the at least one weight, the at least one blood pressure parameter, and the at least one heart rate parameter with higher predictive strength for predicting decompensation relative to the other weight, blood pressure, and heart rate parameters with lower predictive strength.

8. The method of claim 7, further comprising predicting, with the one or more hardware processors, decompensation using the one or more weight parameters, the one or more blood pressure parameters, and the one or more heart rate parameters as feature inputs in a Naïve Bayes classifier.

9. The method of claim 7, wherein the one or more blood pressure parameters include one or more of a systolic blood pressure-based moving average convergence divergence with a long term window size of 40 days and a short term window size of 5 days, a systolic blood pressure-based standard score with a sample length of 20 days, a systolic blood pressure-based standard score with a sample length of 40 days, a change in a mean diastolic blood pressure during an immediately previous week, or a diastolic blood pressure-based standard score with a sample length of 20 days.

10. The method of claim 7, wherein the one or more heart rate parameters include one or more of a change in mean heart rate during an immediately previous month, a heart rate-based moving average convergence divergence with a long term window size of 20 days a and a short term window size of 5 days, a heart rate-based moving average convergence divergence with a long term window size of 40 days and a short term window size of 5 days, or a pulse pressure-based moving average convergence divergence with a long term window size of 20 days and a short term window size of 5 days.

11. The method of claim 7, wherein predicting decompensation includes generating a decompensation risk score that increases with increasing risk of decompensation, and determining whether the decompensation risk score breaches a decompensation risk threshold level.

12. The method of claim 7, wherein the determination of which individual weight, blood pressure, and heart rate parameters have higher predictive strength is made based on changes in the individual weight, blood pressure, and heart rate parameters over time in the subject.

13. A system for predicting decompensation in a subject with heart failure, the system comprising:
means for determining baseline information for the subject based on physiological data of other patients with heart failure, the physiological data of the other patients corresponding to a period of time when the other patients have stable physiological parameters that precedes heart failure;
means for receiving weight information that includes a weight of the subject generated by one or more weight sensors;
means for receiving blood pressure information that includes a blood pressure of the subject generated by one or more blood pressure sensors;
means for receiving heart rate information that includes a heart rate of the subject generated by one or more heart rate sensors;
means for determining one or more weight parameters associated with a change in the weight of the subject based on the weight information with respect to the baseline information;
means for determining one or more blood pressure parameters associated with a change in the blood pressure of the subject based on the blood pressure information with respect to the baseline information;
means for determining one or more heart rate parameters associated with a change in the heart rate of the subject based on the heart rate information with respect to the baseline information;
means for determining individual weight, blood pressure, and heart rate parameters with higher predictive strength for predicting decompensation relative to other weight, blood pressure, and heart rate parameters with lower predictive strength, the individual weight, blood pressure, and heart rate parameters with higher predictive strength comprising at least one predictive weight parameter, at least one predictive blood pressure parameter, and at least one predictive heart rate parameter; and
means for predicting decompensation in the subject based on the at least one weight parameters, the at least one blood pressure, and the at least one heart rate parameter with higher predictive strength for predicting decompensation relative to the other weight, blood pressure, and heart rate parameters with lower predictive strength.

14. The system of claim 13, further comprising means for predicting decompensation using the one or more weight parameters, the one or more blood pressure parameters, and the one or more heart rate parameters as feature inputs in a Naïve Bayes classifier.

15. The system of claim 13, wherein the one or more blood pressure parameters include one or more of a systolic blood pressure-based moving average convergence divergence with a long term window size of 40 days and a short term window size of 5 days, a systolic blood pressure-based standard score with a sample length of 20 days, a systolic blood pressure-based standard score with a sample length of 40 days, a change in a mean diastolic blood pressure during an immediately previous week, or a diastolic blood pressure-based standard score with a sample length of 20 days.

16. The system of claim 13, wherein the one or more heart rate parameters include one or more of a change in mean heart rate during an immediately previous month, a heart rate-based moving average convergence divergence with a long term window size of 20 days a and a short term window size of 5 days, a heart rate-based moving average convergence divergence with a long term window size of 40 days and a short term window size of 5 days, or a pulse pressure-based moving average convergence divergence with a long term window size of 20 days and a short term window size of 5 days.

17. The system of claim 13, wherein predicting decompensation includes generating a decompensation risk score that increases with increasing risk of decompensation, and determining whether the decompensation risk score breaches a decompensation risk threshold level.

18. The system of claim 13, wherein the determination of which individual weight, blood pressure, and heart rate parameters have higher predictive strength is made based on changes in the individual weight, blood pressure, and heart rate parameters over time in the subject.

* * * * *